United States Patent [19]
Fernholz et al.

[11] 3,950,400
[45] Apr. 13, 1976

[54] PROCESS FOR THE OXACYLATION OF OLEFINS IN THE GASEOUS PHASE

[75] Inventors: Hans Fernholz, Fishbach, Taunus; Friedrich Wunder, Florsheim, Main; Hans-Joachim Schmidt, Frankfurt am Main, all of Germany

[73] Assignee: Hoechst Aktiengesellschaft, Frankfurt am Main, Germany

[22] Filed: Nov. 18, 1971

[21] Appl. No.: 200,140

[30] Foreign Application Priority Data
Nov. 20, 1970  Germany............................. 2057087

[52] U.S. Cl............................... 260/497 A; 252/473
[51] Int. Cl.²......................................... C07C 67/04
[58] Field of Search................................ 260/497 A

[56] References Cited
FOREIGN PATENTS OR APPLICATIONS
1,901,289    9/1970    Germany ......................... 260/497 A Primary Examiner—Lorraine A. Weinberger
Assistant Examiner—Michael Shippen
Attorney, Agent, or Firm—Curtis Morris & Safford

[57] ABSTRACT

Improvement of a process for the oxacylation of olefins in the gaseous phase in the presence of carrier catalysts containing palladium salts and additives by adding a barium carboxylic acid aurate the carboxylic acid part of which contains from 2 to 10 carbon atoms.

6 Claims, No Drawings

PROCESS FOR THE OXACYLATION OF OLEFINS IN THE GASEOUS PHASE

This invention relates to a process for the oxacylation of olefins in the gaseous phase.

It is known that olefins can be reacted in the gaseous phase with organic carboxylic acids and oxygen or oxygen containing gases to obtain oxacylation products, for example vinyl acetate, allyl acetate or methallyl acetate. The reaction is carried out in the presence of carrier catalysts containing palladium or palladium salts and other additives, for example gold, gold salts, cadmium, cadmium salts, bismuth, bismuth salts, alkaline earth metal salts or alkali metal salts. Generally, the active components are applied to a porous carrier; such catalyst carriers being for example silicic acid, aluminium oxide, aluminium silicates, titanium oxide, zirconium oxide, silicates, silicium carbide or carbon. Especially suitable are silicic acids having a specific surface of from 40 to 350 m²/g and a mean pore radius of from 50 to 2000 A.

A process for the oxacylation of lower olefins in the gaseous phase, in the presence of carrier catalysts containing palladium salts and additives has now been found, wherein barium carboxylic acid aurates of carboxylic acids having from 2 to 10 carbon atoms, preferably barium aceto-aurate, brium propiono-aurate or barium butyro-aurate are used as additives. Especially advantageous is the use of barium aceto-aurate.

By using these special gold salts, a substantial increase of yield and selectivity of the catalysts is obtained as compared to a simple gold salt, for example tetrachloro-auric acid or auric chloride.

The barium carboxylic acid aurates used in accordance with the present invention are prepared by precipitating aqueous-alkaline aurate solutions with barium hydroxide, by separating the precipitate and dissolving it, while heating, in the corresponding carboxylic acid.

For the preparation for example of barium aceto-aurate, sodium hydroxide solution is added to a dilute auric chloride solution until the precipitate of auric oxide hydrate which is forming is dissolved again. Then the barium aurate is precipitated with saturated barium hydroxide solution until barium hydroxide is present in excess. The precipitate of barium aurate is filtered off, freed from chloride ions by washing with distilled water, and, still in moist state, introduced into acetic acid. This substance is then heated to 80° – 90°C, with agitation, whereby the barium aurate is completely dissolved. While cooling, a crystalline, heavy precipitate of barium aceto-aurate is formed, which, after drying, corresponds to the formula $BaAu_2(CH_3COO)_8$. An analysis yields the following values:

|     | Calculated | Found  |
|-----|------------|--------|
| Ba  | 13.7 %     | 13,5 % |
| Au  | 39.3 %     | 39,6 % |
| AcO⁻| 47 %       | 47 %   |

This barium aceto-aurate is appropriate as additive in accordance with the present invention. It is, however, not necessary to isolate the barium carboxylic acid aurate, since the carboxylic acid solutions obtained can be used also without difficulty for the process of the invention. The amounts of barium carboxylic acid aurates added to the catalysts are from 0.1 to 20% by weight, preferably from 0.2 to 5% by weight of the catalyst system composed of carrier and active components.

The oxacylation itself is carried out by passing carboxylic acid, olefin and oxygen or oxygen containing gases over the catalyst composed of carrier and active components, at temperatures of from 100° to 250°C and pressures of from 1 to 25 absolute atmospheres; non reacted products may be recycled. It is advantageous to use a concentration ratio which ensures that the reaction mixture does not attain the known explosion limits. The simplest way to do this is to keep low the concentration of oxygen, for example at a rate of from 3 to 8% of the gases used. Under certain conditions, also a dilution with inert gases, for example nitrogen or carbon dioxide, may be advantageous. In cyclic processes, especially the latter is appropriate for dilution, since small amounts of it are formed during the reaction.

Suitable carriers are the known inert carrier materials, for example silicic acid, aluminium oxide, aluminium silicates, silicates, titanium oxide, zirconium oxide, titanates, silicium carbide or carbon. Especially advantageous are silicic acids having a specific surface of from 40 to 350 m²/g and a mean pore radius of from 50 to 2000 A.

The catalysts are prepared by impregnating the carriers with a solution of the active components and subsequently drying them. For the oxacylation of ethylene, for example, the carriers are impregnated with a solution of palladium acetate, barium aceto-aurate and potassium acetate in acetic acid, and subsequently dried. A carrier impregnated with an acetic acid solution containing palladium acetate, bismuth acetate, potassium acetate and barium aceto-aurate is appropriate for the oxacylation of propylene to form allyl acetate and of i-butylene to form methallyl acetate. In the case where not acetic acid, but propionic or butyric acid is to be reacted, it is advantageous to use propionates or butyrates instead of acetates.

The olefins used for the process of the invention must be vaporizable under the test conditions. Especially advantageous are ethylene, propylene and i-butylene.

There may be reacted saturated aliphatic, cyclo-aliphatic, araliphatic or aromatic carboxylic acids containing one or more carboxyl groups. It is, however, most important to ensure that the carboxylic acid in question is vaporizable under the reaction conditions; it should therefore contain no more than 10 carbon atoms. Advantageously, unsubstituted, saturated aliphatic monocarboxylic acids having from 2 to 4 carbon atoms, for example propionic acid, n- or i-butyric acid, especially acetic acid, are reacted. Optionally, the carboxylic acids may be used in the form of aqueous solutions.

It is expedient to carry out the reaction in the presence of one or more alkali metal salts of the carboxylic acid which is to be converted. Advantageous are the sodium and potassium salts, the latter being especially preferred. The expedient amounts of alkali metal carboxylates are from 0.1 to 25% by weight, preferably from 1 to 10% by weight, relative to the weight of the catalyst system composed of carrier material and catalytically active substances.

An especially favorable technique is the following; the alkali metal salts of the carboxylic acids are supplied to the catalyst either continuously or discontinuously, the rate of the continuous supply of the alkali metal salts of the carboxylic acids being from 0.1 to 400 ppm, preferably from 1 to 100 ppm, of the carboxylic acid used.

The process of the invention may be carried out in fixed bed reactors, or in fluidization or fluid bed reactors; the fixed bed being generally preferred.

The results of the Examples which demonstrate the advantages of the process of the invention are listed in the following Table:

Space-Time-Yields (S.T.Y.)

| Reaction product | Catalyst containing auric chloride | | Catalyst containing barium aceto-aurate | |
|---|---|---|---|---|
| | S.T.Y. | selectivity | S.T.Y. | selectivity |
| Vinyl acetate | 35 g/l.h | 80% | 240 g/l.h | 94% |
| Allyl acetate | 27 g/l.h | 78% | 280 g/l.h | 97% |
| Methallyl-acetate | 38 g/l.h | 79% | 270 g/l.h | 96% |

This unusual increase of the yields by using barium carboxylic acid aurates is extremely surprising, since in all cases the catalysts contain the same amount of gold.

The following Examples illustrate the invention.

EXAMPLE 1

Preparation of vinyl acetate a. Example using barium aceto-aurate.
450 g of a silicic acid carrier (corresponding to 1 liter) having a specific surface of 190 m²/g and a pore volume of 0.85 ml/g is impregnated with a solution of
  10.7 g of palladium acetate (47.2% of Pd)
  6.5 g of barium aceto-aurate (39.6% of Au)
  46 g of potassium acetate in
340 ml of acetic acid, and dried.
1 Liter of the catalyst is introduced into a reaction tube having an inside diameter of 32 mm, which is connected with a vaporizer before its inlet and a condenser, a receiver and a device for the control of the pressure behind its outlet. At a pressure of 5 atm/gage and a catalyst temperature of 180°C, a gaseous mixture of 870 g of acetic acid, 850 standard liters of ethylene and 75 standard liters of oxygen per hour is passed over the catalyst. Under these conditions, the catalyst yield is 240 g of vinyl acetate per hour, and the selectivity amounts to 94%.

b. Example using a normal gold salt.
450 g of a silicic acid carrier according to that of Example 1a) are impregnated with a solution of
  10.7 g of palladium acetate (47.2% of Pd)
  5.0 g of auric chloride (51.5% of Au)
  46.0 g of potassium acetate
in 340 ml of acetic acid, and dried.
Under the test conditions as described in Example 1a), the condensate contains an average of 35 g of vinyl acetate per hour at a selectivity of 80%.

EXAMPLE 2

Preparation of allyl acetate a. Example using barium aceto-aurate.
450 g of the carrier used in Example 1 a) are impregnated with a solution of
  10.7 g of palladium acetate (47.2% of Pd)
  6.5 g of barium aceto-aurate (39.6% of Au)
  5.9 g of bismuth acetate
  46.0 g of potassium acetate
in 340 ml of acetic acid, and dried.
1 Liter of the catalyst is introduced into the reaction tube described in Example 1a) and, at a pressure of 5 atm/gage and a catalyst temperature of 180°C, 870 g of acetic acid, 850 standard liters of propylene and 75 standard liters of oxygen per hour are passed over the catalyst. Under these conditions, the catalyst yield is 280 g of allyl acetate per hour, and the selectivity amounts to 97%.

b. Example using a normal gold salt.
450 g of the carrier used in Example 1a) are impregnated with a solution of
  10.7 g of palladium acetate (47.2% of Pd)
  5.0 g of auric chloride (51.5% of Au)
  5.9 g of bismuth acetate
  46.0 g of potassium acetate
in 340 ml of acetic acid, and dried.
Under the test conditions described in Example 2a) the condensate contains 27 g of allyl acetate per hour, and the selectivity amounts to 78%.

EXAMPLE 3

Preparation of methallyl acetate a. Example using barium aceto-aurate.
At a pressure of 5 atm/gage and a catalyst temperature of 180°C, 870 g of acetic acid, 850 standard liters of isobutylene and 75 standard liters of oxygen per hour are passed over 1 liter of the catalyst described in Example 2a). In the condensate, 270 g of methallyl acetate per hour are obtained. The selectivity amounts to 96%.

b. Example using a normal gold salt.
1 Liter of the catalyst as described in Example 2a) is used. Under the same test conditions as described in Example 3a), the condensate contains per hour only 38 g of methallyl acetate at a selectivity of 79%.

What is claimed is:

1. In the process for oxacylation of ethylene, propylene or isobutylene in the gaseous phase in the presence of oxygen and a carrier catalyst consisting essentially of palladium salts or palladium salts and as additives therefor alkali and alkaline earth metal salts, gold, gold salts, cadmium, cadmium salts, bismuth, bismuth salts, the improvement consisting essentially of adding a barium carboxylic acid aurate of a carboxylic acid having from 2 to 10 carbon atoms to said carrier catalyst and oxacylating said ethylene, propylene or isobutylene with said catalyst.

2. The process as claimed in claim 1, wherein as barium carboxylic acid aurate barium aceto-aurate is used.

3. The process as claimed in claim 1, wherein as barium carboxylic acid aurate barium propiono-aurate is used.

4. The process as claimed in claim 1, wherein as barium carboxylic acid aurate barium butyro-aurate is used.

5. The process as claimed in claim 1, wherein the amounts of barium carboxylic acid aurates added are from 0.1 to 20% by weight of the system composed of carrier and active components.

6. The process as claimed in claim 1, wherein the amounts of barium carboxylic acid aurates added are from 0.2 to 5% by weight of the system composed of carrier and active components.

* * * * *